United States Patent
Henry et al.

(10) Patent No.: US 7,400,922 B2
(45) Date of Patent: Jul. 15, 2008

(54) MULTI-SITE ACTIVE IMPLANTABLE MEDICAL DEVICE INCLUDING A MODE OF RESYNCHRONIZATION OF THE VENTRICLES

(75) Inventors: Christine Henry, Paris (FR); Marcel Limousin, Paris (FR)

(73) Assignee: ELA Medical S.A.S., Montrouge (FR)

( * ) Notice: Subject to any disclaimer, the term of this patent is extended or adjusted under 35 U.S.C. 154(b) by 84 days.

(21) Appl. No.: 11/012,072

(22) Filed: Dec. 14, 2004

(65) Prior Publication Data

US 2005/0131471 A1 Jun. 16, 2005

(30) Foreign Application Priority Data

Dec. 15, 2003 (FR) .................................. 03 14657

(51) Int. Cl.
*A61N 1/00* (2006.01)
(52) U.S. Cl. .......................................... 607/9; 607/115
(58) Field of Classification Search ................ 607/9
See application file for complete search history.

(56) References Cited

U.S. PATENT DOCUMENTS 5,902,324 A * 5/1999 Thompson et al. ............. 607/9
6,181,968 B1 1/2001 Limousin ..................... 607/28
6,343,231 B1 1/2002 Bouhour et al. ................ 607/9
6,937,901 B2 * 8/2005 Zhu et al. ..................... 607/27
7,096,064 B2 * 8/2006 Deno et al. .................... 607/9
2003/0199934 A1 10/2003 Struble et al. ................. 607/17

FOREIGN PATENT DOCUMENTS

EP 0 488 904 A1 11/1991

* cited by examiner

*Primary Examiner*—Carl H. Layno
*Assistant Examiner*—Brian T Gedeon
(74) *Attorney, Agent, or Firm*—Orrick Herrington & Sutcliffe, LLP

(57) ABSTRACT

An active implantable medical device comprising circuits for right ventricular, left ventricular, right atrial and eventually left atrial detection, as well as circuits for right and left ventricular stimulation. The device can operate in mode of resynchronization of the ventricular contractions, with an adjustable delay of inter-ventricular stimulation. It includes moreover: circuits for atrial stimulation; circuits able to operate the device in AAI mode with right atrial stimulation and right ventricular detection; circuits for detection of ventricular capture, to determine the detection or the loss of capture after a right ventricular stimulation and a left ventricular stimulation; and of the circuits for mode switching, able to control a switching of mode, from the mode of resynchronization towards AAI mode, in response to the detection of a loss of capture after a right ventricular stimulation or a left ventricular stimulation.

6 Claims, 2 Drawing Sheets

MULTI-SITE ACTIVE IMPLANTABLE MEDICAL DEVICE INCLUDING A MODE OF RESYNCHRONIZATION OF THE VENTRICLES

FIELD OF THE INVENTION

The present invention relates to "active implantable medical devices" as defined by the Jun. 20, 1990 directive 90/385/CEE of the Council of the European Communities, and more particularly to cardiac devices such as pacemakers, defibrillators, and/or cardiovertors that are able to deliver to the heart low energy stimulation pulses for treatment of disorders of cardiac rhythm.

BACKGROUND OF THE INVENTION

The invention more particularly relates to "multi-site" prostheses, in which electrodes are placed in a plurality of distinct respective sites comprising the two ventricular sites, right and left, and at least one atrial site. It can be a prosthesis of the "triple chamber" type (double ventricular stimulation and right atrial detection/stimulation) or the "quadruple chamber" type (double ventricular stimulation and double atrial detection/stimulation).

The majority of patients receiving such an implanted multi-site device are patients who usually present a normal atrio-ventricular conduction (each atrial event is followed by an associated ventricular depolarization) and who thus do not have a standard indication for implantation of a permanent pacemaker. The multi-site device is then indicated to treat the cardiac insufficiency so as to improve the general hemodynamic state of these patients, by joint and permanent stimulation of the left and right ventricles in order to re-synchronize them. This therapy makes it possible to observe often spectacular results for patients in class III cardiac insufficiency not improved by traditional treatments. These devices can operate in synchronous stimulation, i.e., the two ventricular sites of stimulation receive at the same time the depolarization impulse (no inter-ventricular delay), or as described in EP-A-1 108 446 and its counterpart, U.S. Pat. No. 6,556,866 (incorporated herein by reference), commonly assigned herewith to ELA Medical, with, between two ventricular stimulations, an inter-ventricular delay adjusted so as to re-synchronize contraction of the ventricles with a fine optimization of the hemodynamic state of the patient.

The starting point of the invention results from clinical observations carried out on patients having received such a device when a loss of capture appears on one of the two ventricular probes. The loss of capture is a situation in which the stimulation impulse applied to the electrode of the probe has an insufficient amplitude to cause depolarization of the ventricle. Such a loss of capture often follows a natural increase, over the long term, of the stimulation threshold. Because of this loss of capture, the stimulation of one of the ventricles will be without effect, and the patient will be in a state with a stimulation of only one of the two ventricles, either right or left. This stimulation of only one ventricle can be extremely noxious, if prolonged, because it can involve an increase in the inter-ventricular desynchronization. The inventors of the present invention noted that, in such a situation, to let express the spontaneous rhythm of the patient can prove to be an alternative less heavy in consequences than to continue stimulation of only one of the ventricles.

OBJECTS AND SUMMARY OF THE INVENTION

Primarily, the invention proposes, in the event of a proven loss of capture on one of the ventricular probes, not to maintain the multi-site mode, but to commutate the device in AAI mode (demand stimulation with the monitoring of the ventricular activity), with possibly later commutation of AAI mode towards a DDD mode (double-chamber stimulation with atrio-ventricular association) in the event of detection of an atrio-ventricular block (AVB).

More precisely, the invention proposes a multi-site device able to function in a mode of ventricular resynchronization of the general type revealed in above mentioned EP-A-1 108 446 and its counterpart, U.S. Pat. No. 6,556,866 (incorporated herein by reference), i.e., a triple or quadruple chamber multi-site device, including: means for right and left ventricular detection, able to detect a potential of spontaneous depolarization in the right ventricle and the left ventricle; means for right atrial detection, and eventually for left atrial detection, able to detect a potential of spontaneous depolarization in the right atrium and in the left atrium; means for right and left ventricular stimulation, able to deliver in the right ventricle and the left ventricle the respective impulses of stimulation; and means able to operate the device in a mode of resynchronization of the ventricular contractions, including means to establish an adjustable inter-ventricular delay between the moments of application of the impulses respectively delivered to the right ventricle and to the left ventricle during the same cardiac cycle.

The device of the invention can also include: means for atrial stimulation, able to deliver impulses of stimulation to the right atrium; means able to operate the device in AAI mode with right atrial stimulation and right ventricular detection; means for detection of ventricular capture, to determine the detection or loss of capture after a right ventricular stimulation and a left ventricular stimulation; and means for mode switching, able to control a switching of mode, from a mode of resynchronization towards the AAI mode, in response to detection of a loss of capture after a right ventricular stimulation or a left ventricular stimulation.

In further embodiments:

- the device can also include means for analyzing the heartbeat rate, able to detect an atrio-ventricular block, and means able to operate the device in double-chamber stimulation DDD mode with atrio-ventricular association, the means for mode switching being also able to control the mode switching from AAI towards DDD mode in the event of detection of an atrio-ventricular block;
- the means for mode switching are also able to control the opposite switching from AAI mode towards the mode of resynchronization in response to detection of a re-establishment of the right and left ventricular capture;
- the means for mode switching include means for applying a predetermined delay before the aforementioned opposite switching from AAI mode towards the mode of resynchronization, after the aforementioned detection of a re-establishment of the right and left ventricular capture;
- the means for mode switching include means for, after opposite switching from AAI mode towards the mode of resynchronization, inhibiting any new later switching from the mode of resynchronization towards the AAI mode for a predetermined length of time.

DETAILED DESCRIPTION OF THE INVENTION

One now will describe an example of realization of the device of the invention, which can be implemented by suitable programming of the control software of a known pacemaker of multi-site type, triple or quadruple chamber including a mode of resynchronization of the ventricles, an AAI mode with monitoring of the ventricular activity and a double-chamber stimulation DDD mode with atrio-ventricular association Suitable devices for which the present invention has application include, for example, the active implantable medical devices available from ELA Medical, Montrouge, France. These devices are microprocessor-based systems having circuits for receiving, conditioning, and processing detected electrical signals, and are capable of receiving software instructions by telemetry, storing them in memory, and then executing those instructions to perform the functions described above in implementing the present invention.

Figure 1:
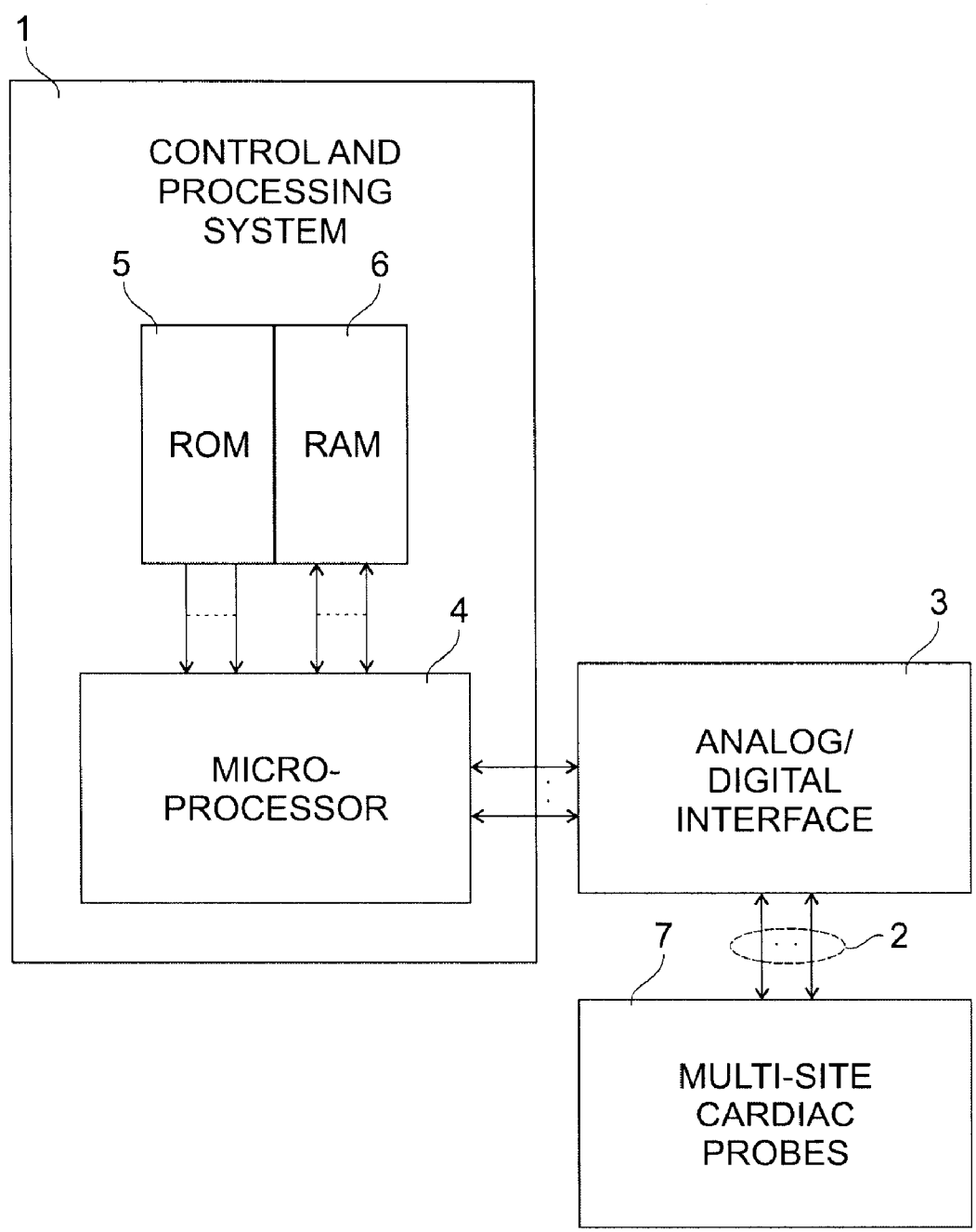
FIG. 1 illustrates schematically the general use of a typical pacemaker of multi-site type.

FIG. 1 illustrates in block form the typical structure of a pacemaker of this type, including a control and processing system 1, multiple leads 2 connected to probes at cardiac sites, an analog/digital interface for transferring the analog signals from the leads 2 to the micro-processor 4 and vice versa, a micro-processor 4 for the processing of instructions necessary in implementing the algorithm of the present invention, ROM 5 and RAM 6 for storing the software instructions and data for implementing the algorithm of the present invention, and cardiac probes 7 placed at multiple cardiac sites as is typical of known multi-site pacemakers. The creation of suitable software instructions for controlling an implant to perform the aforementioned functions of the present invention are within the abilities of a person of ordinary skill in the art. The detection circuits used to detect the cardiac signals in the atrium and the ventricle and the endocardial accelerations signal, in the left and/or right chambers, are well known and any suitable design may be used.

Figure 2:
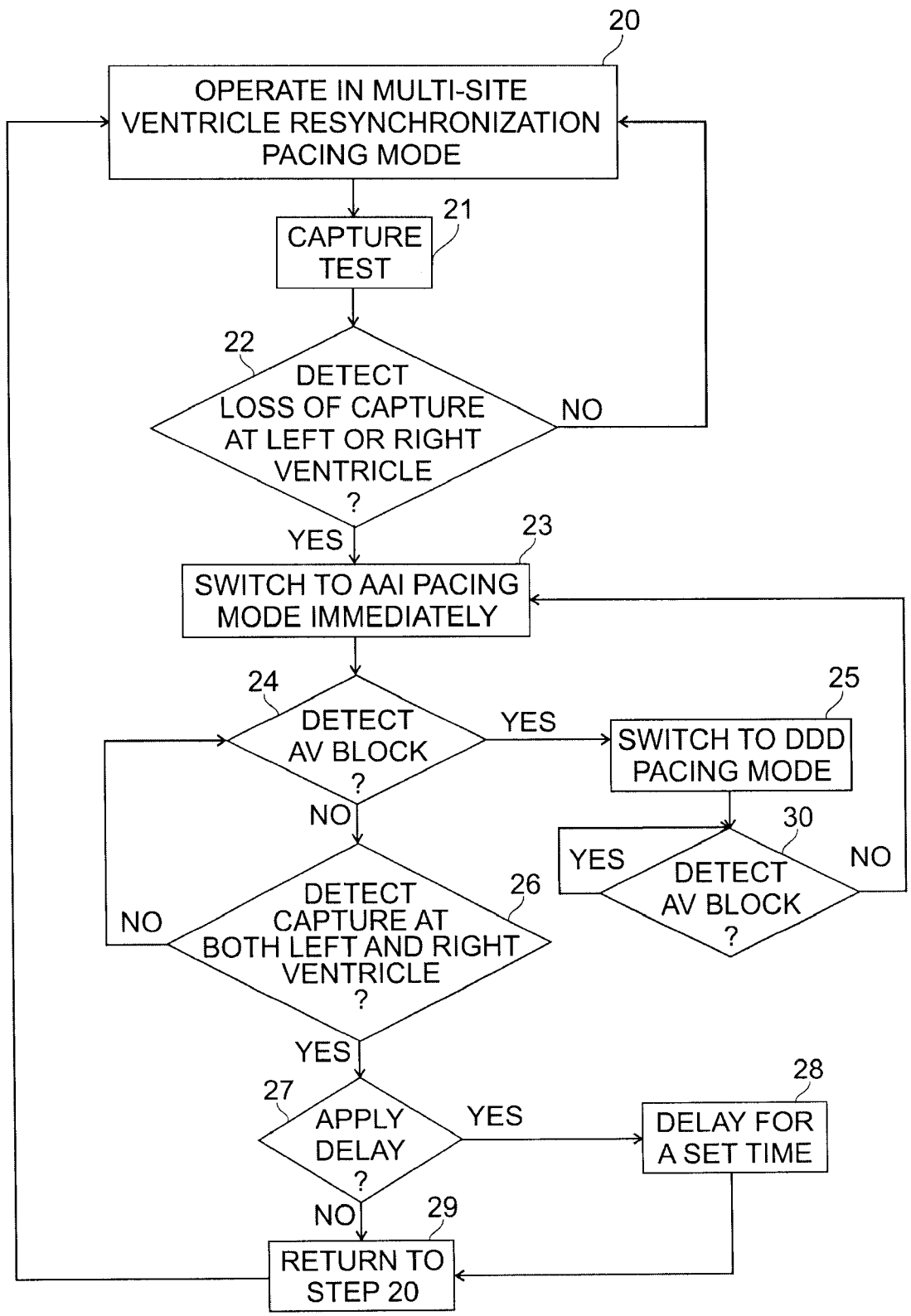
FIG. 2 illustrates a flow chart implementing an algorithm for resynchronizing the ventricles according to the present invention.

One is now going to describe the process of resynchronizing the ventricles according to the present invention, with reference to the flow chart of FIG. 2. At the beginning, the operation of the device is an operation in a ventricular mode of resynchronization (stage 20), i.e., the two ventricular cavities, right and left, are stimulated jointly with an adjusted V-V delay, typically between −60 and +60 ms, at periodic intervals according to hemodynamic parameters measured from outside (e.g., by echography) or uninterrupted by an implanted sensor (e.g., endocavitary acceleration sensor, bio-impedance intracardiac sensor, etc). These techniques of hemodynamic analysis of the state of the patient and of adjustment of parameters of operation of an enslaved (i.e., rate responsive) device are themselves known and need not be described in more detail. One can refer in particular, in addition to the above mentioned EP-A-1 108 446 and its counterpart, U.S. Pat. No. 6,556,866 (incorporated herein by reference), to EP-A-1 116497 and its counterpart, U.S. Pat. No. 6,604,002 (incorporated herein by reference), all commonly assigned herewith to ELA Médical, which expose the manner of collecting a bio-impedance intracardiac signal to vary the inter-ventricular delay of application of the respective impulses of stimulation of the right and left ventricles in the direction of improvement of cardiac flow.

The device of the present invention also includes means to detect possible losses of capture on one of the ventricular probes (stage 21). The algorithms of detection of capture in themselves are well known, and one will be able to refer to EP-A-0 935 979 and its counterpart, U.S. Pat. No. 6,181,968 (incorporated herein by reference), or EP-A-1 287 849 and its counterpart, U.S. Pat. No. 6,714,820 (incorporated herein by reference), all commonly assigned herewith to ELA Medical, this last document in particular describing an algorithm of detection of capture "cycle to cycle", i.e., in which the device examines with each cardiac cycle—and not at periodic intervals—whether stimulation was effective or not.

As shown in stages 22 and 23 of FIG. 2, in a way characteristic of the invention, in the event of proven loss of capture on one of the ventricular probes, the algorithm automatically commutates the device from the initial mode of operation in ventricular resynchronization towards an operating mode of the type AAI, i.e., with an atrial chamber stimulation and a monitoring (detection) of the ventricular activity. This mode makes it possible to let be expressed a normal atrio-ventricular conduction, i.e., where each atrial event (atrial detection corresponding to a spontaneous activity or atrial stimulation) is followed by an associated ventricular detection. In a preferred embodiment, the device allows an operation not only in AAI mode, but also in DDD mode of double chamber stimulation.

The implanted multi-site devices used currently are often devices that include circuits of stimulation and detection at the same time on the atrium and the ventricle and can operate according to two operating modes—DDD and AAI. These devices can in particular be equipped with a mode called "DDD-ACM," ensuring an automatic commutation of the mode (ACM) from DDD to AAI, and conversely.

The basic operating mode of a DDD/AAI pacemaker is an AAI mode, maintained as long as atrio-ventricular conduction is normal (AAI mode being a DDD mode which includes a lengthened atrio-ventricular delay). However, in certain circumstances AVB can appear, involving a temporary disorder of depolarization of the ventricle. In such circumstances, the pacemaker switches automatically to DDD mode (stages 24 and 25), with parameters optimized for this situation of temporary AVB. After disappearance of the AVB, and thus re-establishment of atrio-ventricular conduction, since a certain number of conditions are filled, the pacemaker automatically turns over to AAI mode, as shown in stage 30 of FIG. 2. This commutation between DDD and AAI modes is in particular described in EP-A-0 488 904 and its counterpart, U.S. Pat. No. 5,318,594 (incorporated herein by reference), commonly assigned herewith to ELA Medical and EP-A-1 346 750 and its counterpart, U.S. Patent Application No. 2004010292, also assigned to ELA Medical). Thus, in the event of occurrence of an AVB, and thus of commutation in DDD mode, the pacemaker will find itself concretely in the same type of operation as with the initial ventricular resynchronization mode, induced by the loss of capture on one of the ventricular probes. On the other hand, if the patient does not present a disorder of conduction (absence of AVB and normal atrio-ventricular time), the ventricular rhythm will be able to be expressed spontaneously.

Because the loss of capture may in certain cases be transitory, a test of capture is carried out on regular intervals to detect a possible reappearance of the lost capture, as shown in stage 26. In this last case, i.e., if it is possible to again obtain an effective stimulation on the two ventricles, the device can turn over to the initial mode of ventricular resynchronization, as shown in stage 29. The return to this initial mode can be conditioned with the duration of a certain period, or with the counting of a minimum number of cycles. In the alternative or in addition, as shown in stages 27 and 28, the switching of the system can be then inhibited for a given length of delay, e.g., over four days, in order to avoid multiple commutations of mode over a short period, which could cause disturbances of the rhythm with more serious consequences than simple maintenance of the initial operating mode.

The present invention is completely adapted to "triple chamber" devices, i.e., with probes laid out on the two ventricles and the right atrium. The invention also is applicable to a configuration where the multi-site device comprises probes on the two ventricles and the left atrium, or in "quadruple chamber" configuration, with probes on the two ventricles and the two atriums.

These various configurations can be permanent configurations of the device or, advantageously, configurations modifiable dynamically, as described in EP-A-0 925 806 and its counterpart, U.S. Pat. No. 6,253,106 (incorporated herein by reference), commonly assigned herewith to ELA Medical, where the device can choose and modify the configuration of stimulation so as to optimize treatment of the cardiac insufficiency.

One skilled in the art will appreciate that the present invention can be practiced by other than the described embodiments, which are presented for purposes of illustration and not of limitation.

We claim:

1. An active implantable medical device comprising:
   means for detecting a spontaneous depolarization potential in each of the right ventricle and the left ventricle;
   means for detecting a spontaneous depolarization in the right atrium and eventually in the left atrium;
   means for delivering to each of the right ventricle and the left ventricle impulses of stimulation;
   means for establishing an adjustable inter-ventricular delay between a stimulation impulse delivered to the right ventricle and a stimulation impulse delivered to the left ventricle during a same cardiac cycle;
   means for operating the implantable multi-site pacemaker in a ventricular resynchronization pacing mode that includes a test for capture at both the left and right ventricles;
   means for detecting a loss of capture at either the left or right ventricle;
   means for switching immediately to an AAI pacing mode following a detected loss of capture at either the left or right ventricle;
   means for detecting whether capture has resumed at both the left and right ventricle; and
   means for switching back to the ventricular resynchronization pacing mode if capture has resumed at both the left and right ventricle.

2. The device of claim 1, wherein the switching means further comprises means for inhibiting switching of the device back to the ventricular resynchronization pacing mode for a given length of delay.

3. The device of claim 1, wherein the switching means further comprises means for applying a predetermined delay before switching back to the ventricular resynchronization pacing mode when capture has resumed at both the left and right ventricle.

4. The device of claim 1, wherein the switching means further comprises means for inhibiting, for a predetermined length of time after switching back to the ventricular resynchronization pacing mode from the AAI pacing mode, switching immediately to an AAI pacing mode following a detected loss of capture at either the left or right ventricle.

5. A method for ventricular resynchronization in an implantable multi-site pacemaker device comprising:
   operating the implantable multi-site pacemaker in a ventricular resynchronization pacing mode that includes a test for capture at both the left and right ventricles;
   detecting a loss of capture at either the left or right ventricle;
   switching immediately to an AAI pacing mode following a detected loss of capture at either the left or right ventricle;
   detecting whether capture has resumed at both the left and right ventricle;
   switching back to the ventricular resynchronization pacing mode if capture has resumed at both the left and right ventricle.

6. The method of claim 5, further wherein the switching of the device back to the ventricular resynchronization pacing mode may be inhibited for a given length of delay.

\* \* \* \* \*